United States Patent [19]
Yang

[11] Patent Number: 6,096,332
[45] Date of Patent: Aug. 1, 2000

[54] ADDING PHARMACEUTICALLY ACTIVE COMPOUNDS TO SUBSTRATES

[75] Inventor: Ching-Yun Morris Yang, Princeton Junction, N.J.

[73] Assignee: McNeil-PPC, Inc., Skillman, N.J.

[21] Appl. No.: 09/109,342

[22] Filed: Jun. 30, 1998

[51] Int. Cl.⁷ .................................................. A61F 13/02
[52] U.S. Cl. ............................................................ 424/431
[58] Field of Search ............................................. 424/431

[56] References Cited

U.S. PATENT DOCUMENTS

| | | | |
|---|---|---|---|
| 3,595,236 | 7/1971 | Appleton et al. | 128/285 |
| 3,724,465 | 4/1973 | Duchane | 128/285 |
| 3,756,238 | 9/1973 | Hanke | 128/270 |
| 3,791,902 | 2/1974 | Hanke et al. | 156/212 |
| 3,796,219 | 3/1974 | Hanke | 128/285 |
| 3,821,350 | 6/1974 | Suchane | 264/257 |
| 4,347,237 | 8/1982 | Evenstad et al. | 424/78 |
| 4,582,717 | 4/1986 | von Bittera et al. | 427/2 |
| 4,952,211 | 8/1990 | Snider | 604/285 |
| 4,981,686 | 1/1991 | Hardy | 424/93 |
| 5,417,224 | 5/1995 | Petrus et al. | 128/833 |
| 5,550,145 | 8/1996 | Olund et al. | 514/396 |
| 5,686,097 | 11/1997 | Taskovich et al. | 424/448 |
| 5,753,252 | 5/1998 | Brown-Skrobot | 424/431 |

FOREIGN PATENT DOCUMENTS

| | | |
|---|---|---|
| 0 395 099 A2 | 10/1990 | European Pat. Off. . |
| 0 483 835 A1 | 5/1992 | European Pat. Off. . |
| 0 725 183 A2 | 8/1996 | European Pat. Off. . |
| 2 691 067 | 11/1993 | France . |

*Primary Examiner*—Carlos A. Azpuru

[57] ABSTRACT

The present invention relates to a low temperature process for adding pharmaceutically active compounds to substrates. The substrates are preferably those used in the manufacture of disposable absorbent articles, or are the articles themselves. The pharmaceutically active compound is selected from the group consisting of: monoesters of a polyhydric aliphatic alcohol and a fatty acid containing from eight to eighteen carbon atoms and wherein said monoester has at least one hydroxyl group associated with its aliphatic alcohol residue; diesters of a polyhydric aliphatic alcohol and a fatty acid containing from eight to eighteen carbon atoms and wherein said diester has at least one hydroxyl group associated with its aliphatic alcohol residue; and mixtures of said monoesters and diesters.

15 Claims, No Drawings

//ADDING PHARMACEUTICALLY ACTIVE COMPOUNDS TO SUBSTRATES

BACKGROUND OF THE INVENTION

The present invention relates to a process for adding pharmaceutically active compounds to substrates. The present invention is particularly useful for substrates used in the manufacture of disposable absorbent articles, specifically suited for substrates used in the manufacture of tampons.

There are several methods of delivering pharmaceutically active compounds to their intended targets, including but not limited to oral, topical, and transdermal. Disposable absorbent articles can be used as vehicles for topical delivery to the vaginal canal, perineum, and related areas, as well as for treatment sites for the discharged fluids to come in contact with the pharmaceutically active compounds, as they are captured by the product.

Duchane, U.S. Pat. No. 3,796,219, discloses a water-soluble, thermoplastic composition for hygienic and medical applications, such as for use as an insertion aid coating for tampons and as the matrix structure for suppositories. The coating is stable in temperatures up to 65° C., and it provides lubricity at temperatures below 65° C. when exposed to shear forces, such as those present during insertion of the tampon. Duchane discloses the use of two olefinic diols, polyethylene glycol and propylene glycol in combination with hydroxypropyl cellulose (HPC) having a molecular weight of approximately 75,000. The resulting composition is stable at temperatures up to 65° C. Von Bittera et al., U.S. Pat. No. 4,582,717, discloses a process for producing vaginal tampons containing a pharmaceutically active compound. The process involves preparing a material containing the active compound and additional formulation auxiliaries, heating the material to a temperature in excess of 40° C., cooling the melt to 40° C., and then injecting the cooled material into pre-warmed tampons. One of the formulation auxiliaries disclosed in von Bittera is polyethylene glycol (PEG) having moderate molecular weight. A common theme of the art shown above is the attempt to provide a coating that is stable above room temperature, but is liquid at or near body temperature (37° C.). Brown-Skrobot, U.S. Pat. No. 5,679,369, discloses additives to tampons to inhibit the production of toxic shock syndrome toxin-1. The additives generally are not liquid at or near room temperature, and therefore, they require a carrier material, such as isopropyl alcohol. This technology represents an important advance in the art, but the disclosed process of applying the additive may require a recovery process to capture the volatile alcohol.

All of the art above requires either the use of significant energy or a volatile carrier material, to apply their respective coatings; thus a need still exists for a process for adding pharmaceutically active compounds to substrates or articles of manufacture, without the limiting requirements as stated.

SUMMARY OF THE INVENTION

The present invention relates to a solution of an olefinic diol and a pharmaceutically active compound that is liquid at a temperature of less than about 35° C., to the solution's preparation, and to its use. This solution is useful in low temperature addition of the pharmaceutically active compound to articles of manufacture. In accordance with one embodiment of the present invention, the solution is applied to a substrate at a temperature of less than 40° C. In another embodiment of the present invention, the solution is applied to a disposable absorbent article at a temperature of less than 40° C. A third embodiment involves applying the solution to a fluid permeable material at a temperature of less than 40° C. and encasing at least a portion of an absorbent material with the fluid permeable material. The invention also relates to a disposable absorbent article containing an additive, wherein the additive comprises the solution described above.

The pharmaceutically active compound of the present invention is selected from the group consisting of:

i) monoesters of a polyhydric aliphatic alcohol and a fatty acid containing from eight to eighteen carbon atoms and wherein said monoester has at least one hydroxyl group associated with its aliphatic alcohol residue;

ii) diesters of a polyhydric aliphatic alcohol and a fatty acid containing from eight to eighteen carbon atoms and wherein said diester has at least one hydroxyl group associated with its aliphatic alcohol residue; and iii) mixtures of said monoesters and diesters.

DETAILED DESCRIPTION OF THE INVENTION

The present invention relates to a low temperature process for adding pharmaceutically active compounds to substrates, specifically substrates used in the manufacture of disposable absorbent articles, to the articles during manufacture, or to the finished product. The process incorporates the use of a liquid solution to apply the active compound to substrates. The solution of the present invention is liquid at a temperature of less than about 35° C., and it comprises an olefinic diol as a solvent, and a chosen pharmaceutically active compound as a solute. One advantage the present invention provides is the ability to apply pharmaceutically active compounds to substrates at low temperatures. The advantage eliminates the need for applying significant energy to the active compound for application, resulting in energy cost savings; equipment cost savings, and other related items. The present invention also eliminates the need for a volatile carrier for the pharmaceutically active compound and for a system to recover such a carrier. As used in this specification and the appended claims, liquid is defined to be a substance that has a definite volume but no definite form except such as given by its container. A solution is defined herein to be a homogeneous mixture of a substance (solid, liquid, or gas) dissolved in a liquid, the solvent.

A second advantage provided by the present invention is the reduced volatility of the pharmaceutically active compound during processes at elevated temperatures. As energy is applied to a substrate containing the solution, the solution may begin to volatilize. During this volatilization, the vapor pressure of the solution is made up of the partial pressures of each component in the solution. This is governed by Raoult's law, which states that the partial pressure of any component in the vapor is equal to its mole fraction in the solution times the vapor pressure of the pure component at the same temperature. Therefore, at a given temperature, the vapor driven off of a solution will contain less of the active compound than if it were exposed neat, without the solvent. Many substrates, such as through-air bonded or thermally bonded nonwovens, are subjected to thermal energy during their manufacture. If the fibers used to form such nonwovens have already been finished with the solution of the present invention, then less of the active compound will be lost during the formation of the nonwoven. More of the pharmaceutically active compound will be available for its intended purpose. As evidence of this phenomenon, glycerol monolaurate ("GML"), a preferred pharmaceutically active compound of the present invention, was added neat to Dish 1, while a 50:50 ratio solution of GML in PEG-400 (polyethylene glycol, having an average molecular weight (number average) of 400) was added to Dish 2. Both dishes were heated at a temperature of about 120° C. for 20 minutes. The results are shown in Table 1 below.

TABLE 1

|        | Initial Weight (g) | Final Weight (g) | Weight loss (g) | % loss GML* |
|--------|--------------------|------------------|-----------------|-------------|
| Dish 1 | 0.4204             | 0.4068           | 0.0136          | 3.23        |
| Dish 2 | 0.8557             | 0.8476           | 0.0081          | 1.89        |

*Assuming all weight loss attributable to GML

Assuming the worst case scenario, i.e., all of the loss was attributed to the GML, the results show that less of the pharmaceutically active compound will volatize from a solution than from the neat compound. A third advantage is the improved adherence of the pharmaceutically active compound to a substrate. For example, a solution of GML in PEG-400 may be more compatible with a fibrous structure comprising polyolefin fibers than the GML alone. This is believed to occur due to the chemical structure of PEG-400. This compound has similar structure to both the glycerol portion of GML or other of the polyhydric aliphatic alcohols and to the olefin fiber. It is believed that the olefinic diol, e.g., PEG-400, acts as a coupling agent from the pharmaceutically active compound and the substrate. Therefore, it is believed that the solution of the present invention is especially effective with substrates comprising polyolefins.

Yet another advantage of the present invention is that the solution creates a more wettable structure than a structure having a pharmaceutically active compound that is hydrophobic or only moderately hydrophilic. When these compounds are applied to a substrate, these properties are then transferred to the resulting structure. If a hydrophobic substrate is used as a liquid permeable cover material in a disposable absorbent article, then the product's performance may be reduced. That is, a hydrophobic or moderately hydrophilic cover may inhibit fluid transfer through it and into the absorbent material. The addition of the olefinic diol yields a more hydrophilic solution, and therefore, a more hydrophilic substrate.

A material is defined to be hydrophobic if a water droplet placed onto the surface of the material yields a contact angle of greater than 90□, as measured according to a standard test method, such as ASTM D 5725: "Surface Wettability and Absorbency of Sheet Materials Using on Automated Contact Angle Tester."

A material is moderately hydrophilic if it yields a contact angle of between 30□ and 90□, and highly hydrophilic having a contact angle of less than 30□. As used in this specification and in the appended claims, wettable is defined to be a material that is moderately or highly hydrophilic.

The olefinic diols of the present invention are highly hydrophilic and/or very miscible with water. Thus, aqueous bodily fluids that may be absorbed by absorbent structures treated with the present solution will have a greater affinity for such structures than for structures treated with the neat pharmaceutically active compound. A representative, non-limiting list of olefinic diols useful in the present invention includes the following: polyethylene glycol, polypropylene glycol, polybutylene glycol, propylene glycol, and the like. The olefinic diols of the present invention are liquid at a temperature of less than about 35° C. This weight is typically dictated by their molecular weight. As used herein in the specification and claims, the term "molecular weight" refers to the number average molecular weight of a sompound. Preferably, the olefinic diol is polyethylene glycol, having a molecular weight of less than about 600, or polypropylene glycol, having a molecular weight of less than about 4,000. More preferably, the solvent used in the present invention is polyethylene glycol, having an average molecular weight of less than about 600.

The pharmaceutically active compounds useful in the present invention used in the present invention are useful to inhibit the production of toxins by various bacteria as disclosed in Brown-Skrobot and Brown-Skrobot et al., U.S. Pat. Nos. 5,389,374; 5,547,985; 5,641,503; 5,679,369; and 5,705,182, all of which are herein incorporated by reference. These compounds are selected from the group consisting of: monoesters of a polyhydric aliphatic alcohol and a fatty acid containing from eight to eighteen carbon atoms and wherein said monoester has at least one hydroxyl group associated with its aliphatic alcohol residue; diesters of a polyhydric aliphatic alcohol and a fatty acid containing from eight to eighteen carbon atoms and wherein said diester has at least one hydroxyl group associated with its aliphatic alcohol residue; and mixtures of said monoesters and diesters. Preferably, the active compound is glycerol monolaurate.

The solution of the present invention may be prepared by dissolving a pharmaceutically active compound with a suitable olefinic diol. The order of adding the solvent and solute is not critical to the present invention.

Optionally, a slight amount of energy can be utilized for preparing the solution in an effort to decrease the amount of time needed to render a homogenous solution. The solution ratio of low molecular weight olefinic diol to pharmaceutically active compound, useful in the present invention, is from about 5:95 to about 95:5; preferably, from about 20:80 to about 80:20; and most preferably, from about 60:40 to about 70:30.

After the solution is prepared, in accordance to the description above, it is then applied to a substrate. Useful substrates include, but are not limited to absorbent and non-absorbent fibers, such as cellulose, rayon, polyester, polyethylene, polypropylene, ethylene vinyl acetate, polyurethane, and the like; non-woven fabrics, such as spunbonded fabric, thermal bonded fabric, resin bonded fabric, and the like; apertured and non-apertured films; foams, such as polyurethane foams; and superabsorbent polymers, such as polyacrylic acid, and the like. Preferably, the solution is applied to a nonwoven fabric or its precursor fiber(s), wherein the nonwoven comprises thermally bonded synthetic fibers, such as polypropylene and polyester/ polyethylene bicomponent fibers. The solution provided by the present invention is especially compatible with substrates comprising olefinic materials. The process of applying the solution is by any number of methods known by one skilled in the art, such as roller transfer coating, spray, dip, and the like.

The amount of pharmaceutically active compound applied to a substrate, useful in the present invention, is from about 0.1 to about 2.0 weight percent; preferably, from about 0.1 to about 1.0 weight percent; and most preferably, from about 0.1 to about 0.3 weight percent. The amount of solution applied to the substrate, determined from the preferred solution ratios and amount of pharmaceutically active compound, is from about 0.2 weight percent to about 40 weight percent; preferably, from about 0.2 weight percent to about 20 weight percent; and most preferably, from about 0.2 weight percent to about 6.0 weight percent.

The substrates of the present invention can be used independently, or as an element in the manufacture of disposable absorbent articles. Such articles can include patches for topical or transdermal applications, nasal pads (nasal tampons), diapers, incontinence products, sanitary protection products, body wipes, bedsheets and surgical gowns. Preferably, the substrates are elements in used in the manufacture of sanitary protection. The solutions can also be applied to finished disposable absorbent articles.

Typically, sanitary protection articles fall into two distinct categories, those worn externally in contact with the perineum and those worn internally, partially or wholly contained within the vaginal canal. External sanitary protection products include, without limitation, pantiliners, full-size pads, and ultrathins.

Internal sanitary protection products can be defined as absorbing products, such as sanitary tampons, and the like; collecting products, such as described in Contente et al., U.S. Pat. No. 5,295,984 and the like; or a combination of the two. U.S. Pat. No. 4,294,253 and 4,642,108, incorporated by reference herein, disclose tampon constructions and processes of manufacture. A preferred disposable absorbent article of the present invention, for the solution to be applied to, is a sanitary tampon.

A process for producing disposable absorbent articles comprises encasing at least a portion of an absorbent material with a liquid permeable material, wherein the discharged fluids, contact and penetrate the liquid permeable material, and are drawn into the absorbent material for storage. The liquid permeable material may be a nonwoven fabric such as a spunbonded fabric, a thermal bonded fabric, a resin bonded fabric, and the like; a three-dimensional or two-dimensional apertured polymeric film; or any other suitable covering surface that is capable of allowing fluid to permeate and be comfortably worn against the perineum. A representative, non-limiting list of materials useful as the absorbent material includes cellulosic fibers, such as wood pulp and cotton pulp; synthetic fibers, such as polyesters and polyolefins; superabsorbent polymers, such as polyacrylic acid, and the like.

Optionally, the process can further comprise encasing a second portion of the absorbent material with a liquid impermeable material, to prevent the collected fluid from transferring completely through the article. Useful liquid impermeable materials include, without limitation, polymeric films or coatings, such as polyolefins (e.g., polyethylene and polypropylene), polyvinyls (e.g., polyvinyl acetate, polyvinyl chloride, and poyvinylidene chloride), copolymers (e.g., ethylene vinyl acetate), and blends or laminates of one or more of the above polymers; bodily fluid repellant structures such as nonwovens, apertured films, and repellant fiber layers integrated into the bottom layer of the absorbent materials.

The invention has been illustrated by, but is not intended to be limited to, the above description and examples. The scope of the invention is to be determined by the claims attached hereto.

What is claimed is:

1. A low temperature process for the production of substrates containing pharmaceutically active compounds, comprising the following steps:
    a) preparing a solution of an olefinic diol and a pharmaceutically active compound, which is selected from the group consisting of:
        i) monoesters of a polyhydric aliphatic alcohol and a fatty acid containing from eight to eighteen carbon atoms and wherein said monoester has at least one hydroxyl group associated with its aliphatic alcohol residue;
        ii) diesters of a polyhydric aliphatic alcohol and a fatty acid containing from eight to eighteen carbon atoms and wherein said diester has at least one hydroxyl group associated with its aliphatic alcohol residue; and
        iii) mixtures of said monoesters and diesters;
    wherein the solution is liquid at a temperature of less than about 35° C.; and
    b) applying the solution to the substrate at a temperature of less than 40° C.

2. The process of claim 1 wherein the substrate contains a solution add-on level of less than about 40 wt-%.

3. The process of claim 1 wherein the pharmaceutically active compound is glycerol monolaurate.

4. The process of claim 1 wherein the solution is prepared to have a ratio of olefinic diol to pharmaceutically active compound from about 5:95 to about 95:5.

5. The process of claim 1 wherein the olefinic diol is polyethylene glycol, having an average molecular weight of less than about 600.

6. The process of claim 1 wherein the olefinic diol is polypropylene glycol, having an average molecular weight of less than about 4,000.

7. The process of claim 1 wherein the substrate comprises fibers.

8. The process of claim 1 wherein the substrate comprises a foam.

9. The process of claim 1 wherein the substrate comprises a polymeric film.

10. The process of claim 9 wherein the polymeric film is apertured.

11. The process of claim 1 wherein the substrate comprises a polyolefin.

12. A process for the production of a disposable absorbent article containing pharmaceutically active compounds, comprising the following steps:
    a) preparing a solution of an olefinic diol and a pharmaceutically active compound selected from the group consisting of:
        i) monoesters of a polyhydric aliphatic alcohol and a fatty acid containing from eight to eighteen carbon atoms and wherein said monoester has at least one hydroxyl group associated with its aliphatic alcohol residue;
        ii) diesters of a polyhydric aliphatic alcohol and a fatty acid containing from eight to eighteen carbon atoms and wherein said diester has at least one hydroxyl group associated with its aliphatic alcohol residue; and
        iii) mixtures of said monoesters and diesters;
    wherein the solution is liquid at a temperature of less than about 35° C.; and
    b) applying said solution to the disposable absorbent article at a temperature of less than 40° C.

13. The process of claim 12 wherein the disposable absorbent article comprises a polyolefin.

14. A process for the production of disposable absorbent article containing pharmaceutically active compounds, comprising the following steps:
    a) preparing a solution of an olefinic diol and a pharmaceutically active compound selected from the group consisting of:

i) monoesters of a polyhydric aliphatic alcohol and a fatty acid containing from eight to eighteen carbon atoms and wherein said monoester has at least one hydroxyl group associated with its aliphatic alcohol residue;

ii) diesters of a polyhydric aliphatic alcohol and a fatty acid containing from eight to eighteen carbon atoms and wherein said diester has at least one hydroxyl group associated with its aliphatic alcohol residue; and iii) mixtures of said monoesters and diesters;

wherein the solution is liquid at a temperature of less than about 35° C.;

b) applying said solution to a fluid permeable material at a temperature of less than 40° C.; and c) encasing at least a portion of an absorbent material with the fluid permeable material.

15. The process of claim 14 wherein the disposable absorbent article comprises a polyolefin.

\* \* \* \* \*